US012268842B2

(12) United States Patent
Gaetano et al.

(10) Patent No.: US 12,268,842 B2
(45) Date of Patent: *Apr. 8, 2025

(54) SEMI-AUTONOMOUS HOT-SWAP INFUSION MODULE

(71) Applicant: CareFusion 303, Inc., San Diego, CA (US)

(72) Inventors: Jeffrey L. Gaetano, San Diego, CA (US); Gregory Borges, San Diego, CA (US); Eugene A. Rozell, San Diego, CA (US); Mark P. Bloom, Chula Vista, CA (US); Mooneer T. Salem, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/239,078

(22) Filed: Aug. 28, 2023

(65) Prior Publication Data

US 2023/0398291 A1 Dec. 14, 2023

Related U.S. Application Data

(63) Continuation of application No. 17/579,473, filed on Jan. 19, 2022, now Pat. No. 11,738,141, which is a
(Continued)

(51) Int. Cl.
*G08B 21/04* (2006.01)
*A61M 5/168* (2006.01)
(Continued)

(52) U.S. Cl.
CPC ........ *A61M 5/16831* (2013.01); *A61M 5/172* (2013.01); *G16H 20/17* (2018.01);
(Continued)

(58) Field of Classification Search
USPC ........ 340/539.12, 539.24, 545.3, 568.1, 571, 340/573.1, 641, 691.2, 691.6, 5.52, 5.91
See application file for complete search history.

(56) References Cited

U.S. PATENT DOCUMENTS 6,272,370 B1 8/2001 Gillies
8,275,438 B2 * 9/2012 Simpson ............. A61B 5/4839
600/347

(Continued)

FOREIGN PATENT DOCUMENTS

AU 2011383571 A1 7/2014
CN 101743548 A 6/2010
(Continued)

OTHER PUBLICATIONS

Australian Office Action for Application No. 2019257635, dated Nov. 30, 2023, 5 pages.
(Continued)

*Primary Examiner* — Daniel Previl
(74) *Attorney, Agent, or Firm* — Morgan, Lewis & Bockius LLP

(57) ABSTRACT

A method that includes receiving, in a medication delivery module, a command to start a medication delivery from a first control module coupled to the medication delivery module, is provided. The command to start the medication delivery is based on clinical information received at the first control module. The method includes recording, in a memory of the medication delivery module, an update of the medication delivery, receiving an indication that the medication delivery module was decoupled from the first control module, and receiving an indication that the medication delivery module has become coupled with a second control module. The method also includes communicating, in response, with the second control module, to update the clinical information. A system and a non-transitory, com-
(Continued)

puter readable medium storing instructions to perform the above method are also provided.

20 Claims, 7 Drawing Sheets

Related U.S. Application Data continuation of application No. 15/963,381, filed on Apr. 26, 2018, now Pat. No. 11,278,670.

(51) Int. Cl.
*A61M 5/172* (2006.01)
*G16H 20/17* (2018.01)
*A61M 5/36* (2006.01)

(52) U.S. Cl.
CPC ... *A61M 2005/16868* (2013.01); *A61M 5/365* (2013.01); *A61M 2205/18* (2013.01); *A61M 2205/3368* (2013.01); *A61M 2205/3584* (2013.01); *A61M 2205/52* (2013.01); *A61M 2205/583* (2013.01); *A61M 2205/6009* (2013.01); *A61M 2205/70* (2013.01)

(56) References Cited

U.S. PATENT DOCUMENTS

| | | | |
|---|---|---|---|
| 8,562,528 B2* | 10/2013 | Leach | A61B 5/14535 600/347 |
| 9,695,403 B2 | 7/2017 | Weiner | |
| 10,238,799 B2 | 3/2019 | Kohlbrecher | |
| 10,842,932 B1* | 11/2020 | Bibian | A61M 5/1684 |
| 11,278,670 B2* | 3/2022 | Gaetano | A61M 5/16831 |
| 11,738,141 B2* | 8/2023 | Gaetano | G16H 20/17 705/2 |
| 2005/0171815 A1 | 8/2005 | Vanderveen | |
| 2006/0047538 A1 | 3/2006 | Condurso | |
| 2007/0185615 A1 | 8/2007 | Bossi | |
| 2008/0035520 A1 | 2/2008 | Caracciolo | |
| 2008/0059228 A1 | 3/2008 | Bossi | |
| 2010/0049012 A1 | 2/2010 | Dijksman | |
| 2013/0173277 A1 | 7/2013 | Eller | |
| 2014/0005743 A1 | 1/2014 | Giuffrida | |
| 2014/0039383 A1 | 2/2014 | Dobbles | |
| 2014/0074180 A1 | 3/2014 | Heldman | |
| 2014/0278458 A1 | 9/2014 | Borges et al. | |
| 2015/0057518 A1 | 2/2015 | Lebel et al. | |
| 2015/0119689 A1 | 4/2015 | Pascual-Leone | |
| 2016/0051750 A1 | 2/2016 | Tsoukalis | |
| 2017/0173262 A1 | 6/2017 | Veltz | |

FOREIGN PATENT DOCUMENTS

| | | |
|---|---|---|
| CN | 103210392 A | 7/2013 |
| CN | 106056509 A | 10/2016 |
| CN | 106663139 A | 5/2017 |
| EP | 3107601 A1 | 12/2016 |
| JP | 2000-042102 A | 2/2000 |
| JP | 2012-205737 A | 10/2012 |
| JP | 2017-526470 A | 9/2017 |
| KR | 20030088032 | 11/2003 |
| KR | 20170016335 A | 2/2017 |
| WO | WO 2016/157655 A1 | 10/2016 |

OTHER PUBLICATIONS

Chinese Office Action for Application No. 201980040576.1, dated Sep. 28, 2023, 14 pages including English translation.
European Office Action for Application No. 19727135.6, dated Dec. 13, 2023, 7 pages.
Chinese Office Action for Application No. 2020-559517, dated Jan. 20, 2023, 4 pages including English translation.
International Search Report and Written Opinion for Application No. PCT/US2019/028561, dated Jul. 31, 2019, 20 pages.
Korean Office Action for Application No. 10-2020-7033605, dated Dec. 27, 2021, 12 pages including translation.
Australian Office Action for Application No. 2019257635, dated Jun. 18, 2024, 4 pages.

* cited by examiner

SEMI-AUTONOMOUS HOT-SWAP INFUSION MODULE

CROSS-REFERENCE TO RELATED APPLICATIONS

This application is a continuation of U.S. application Ser. No. 17/579,473, entitled "SEMI-AUTONOMOUS HOT-SWAP INFUSION MODULE," filed Jan. 19, 2022, now U.S. Pat. No. 11,738,141, which is a continuation of application Ser. No. 15/963,381, entitled "SEMI-AUTONOMOUS HOT-SWAP INFUSION MODULE," filed on Apr. 26, 2018, now U.S. Pat. No. 11,278,670, the entirety of each of which is incorporated herein by reference for all purposes.

TECHNICAL FIELD

The present disclosure is generally related to apparatus and methods for medication delivery through an infusion system (IS). More specifically, the present disclosure relates to an apparatus and methods for swapping control modules for an infusion pump during medication delivery.

BACKGROUND

Many approaches to fluid delivery involve relocating a medication delivery module from a first control module to an alternate control module due to any of multiple contingencies that may occur during an infusion process. Especially for non-scheduled contingencies, it may be desirable to transfer a medication delivery module from the first control module to a second control module and to avoid loss of data, of time, and to prevent medication errors while doing so. In some configurations, it is desirable to unplug a medication delivery module from an IS (e.g., while re-arranging the IS configuration, or moving the patient), while the medication delivery module continues to deliver medication. Under current technology, infusion information is recovered after a brief pause in the infusion when rearranging pumps on a single control module, where ideally there would be no interruption or loss of information when rearranging on a single control module, or attachment to a second control module.

SUMMARY

In a first implementation, a computer-implemented method includes receiving, in a medication delivery module, a command to start a medication delivery from a first control module electronically coupled to the medication delivery module, the command to start the medication delivery based on clinical information received at the first control module, initiating, by the medication delivery module, the medication delivery according to the clinical information, updating, in a memory of the medication delivery module, during the medication delivery, delivery information for the medication delivery; receiving, before the medication delivery is completed, a first indication that the medication delivery module was decoupled from the first control module, receiving, after the first indication, a second indication that the medication delivery module has become electronically coupled with a second control module, and communicating, by the medication delivery module, in response to receiving the second indication, the previous, accurate or most recent delivery information to the second control module. Other aspects include corresponding systems, apparatus, and computer program products for implementation of the method.

In some implementations a system includes a memory storing instructions and one or more processors coupled with the memory and configured to execute the instructions to cause the system to receive, using a medication delivery module, a command to start a medication delivery from a first control module, the command to start the medication delivery based on clinical information, initiate, using the medication delivery module, the medication delivery according to the clinical information, update, during the medication delivery, delivery information for the medication delivery, receive, before the medication delivery is completed, a first indication that the medication delivery module was decoupled from the first control module, receive, after the first indication, a second indication that the medication delivery module became electronically coupled with a second control module, and communicate, based on the second indication, the clinical information and the updated delivery information to the second control module. Other aspects include corresponding apparatus, methods, and computer program products for implementation of the system.

In further implementations, a non-transitory, computer-readable medium stores instructions which, when executed by a processor in a computer, cause the computer to perform a method. The method includes receiving, by a medication delivery module, a command to start a medication delivery from a first control module, the command to start the medication delivery based on a clinical information, initiating, by the medication delivery module, the medication delivery according to the clinical information, storing a record of the medication delivery in a non-transitory memory medium of the medication delivery module, receiving, before the medication delivery is completed, a first indication that the medication delivery module was decoupled from the first control module, continuing the medication delivery while the medication delivery module is decoupled from the first control module, updating, while the medication delivery module is decoupled from the first control module, the record of the medication delivery in a non-transitory memory medium of the medication delivery module, receiving, after the first indication, a second indication that the medication delivery module was electronically coupled to a second control module, and communicating, after the second indication, the clinical information and the updated record of the medication delivery to the second control module. Other aspects include corresponding systems, apparatus, methods, and computer program products for implementation of the computer-readable medium.

BRIEF DESCRIPTION OF THE DRAWINGS

In the figures, elements having the same or similar reference numeral have the same or similar functionality or configuration, unless expressly stated otherwise.

DETAILED DESCRIPTION

The present disclosure provides implementations to perform a seamless swap of infusion control modules for an infusion pump during an infusion process. Some of the advantages of implementations consistent with the present disclosure include a smooth and continuous transition from a first control module to a second control module, without any loss of data and largely eliminating any medication infusion alterations, or minimizing any desirable user actions during the transition. Implementations as disclosed herein are suitable for emergency situations when a rapid action is desirable, e.g., when an infusion control module stops working, or network communication with the infusion pump is lost due to a system malfunction, a device malfunction, or an unexpected patient re-location. In that regard, an infusion control module swap may be scheduled when a patient is relocated from a first area in a hospital to a second area, wherein a first infusion control module may remain fixed to the first area, and a second infusion control module may re-take control over the infusion process when the infusion pump arrives in the second area.

Figure 1:
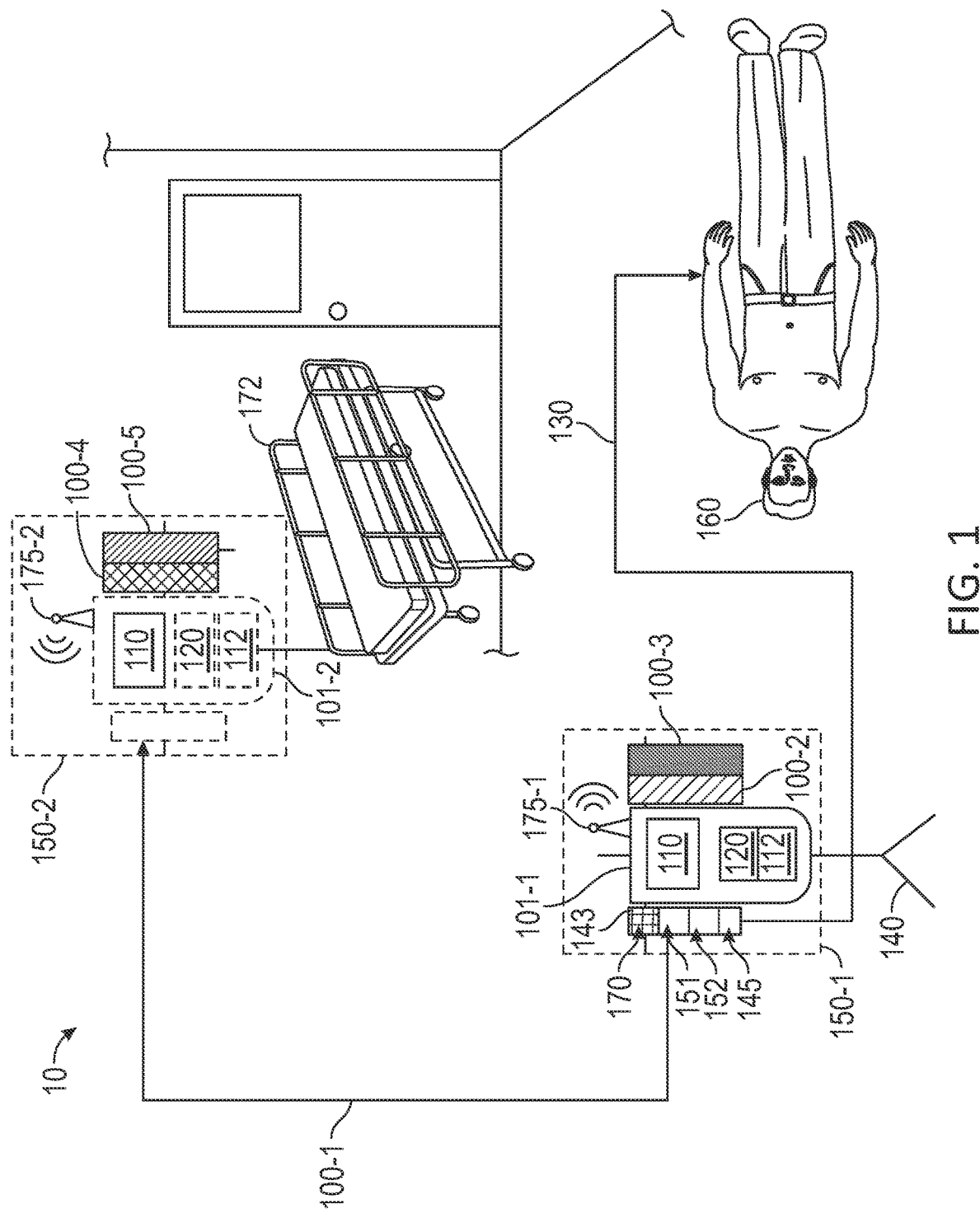
FIG. 1 illustrates a medication delivery system configured to deliver medication to a patient, according to some implementations.

FIG. 1 illustrates a medication delivery system 10 configured to deliver medication to a patient 160. Medication delivery system 10 includes a first infusion system (IS) IS 150-1 installed on a rack 140, and a second IS 150-2 installed on a gurney 172. Hereinafter, IS 150-1 and IS 150-2 will be collectively referred to as "ISs 150." IS 150-1 may include medication delivery modules 100-1, 100-2, 100-3 attached to a control module 101-1, and IS 150-2 may include medication delivery modules 100-4, and 100-5 attached to a control module 101-2. Hereinafter, medication delivery modules 100-1 through 100-5 will be collectively referred to as "medication delivery modules 100," and control modules 101-1 and 101-2 will be collectively referred to as "control modules 101." In some implementations, the operation of each one of medication delivery modules 100 is controlled by a control module 101 to which it is attached. For example, control module 101-1 may send instructions to medication delivery modules 100-1, 100-2 and 100-3 regarding a medication delivery to a patient in the patient's room (IS 150-1). Similarly, control module 101-2 controls medication delivery modules 100-4 and 100-5 on gurney 172 (IS 150-2). Accordingly, after receiving instructions from control module 101, IS 150-2 may be configured to continue a medication delivery when patient 160 is transported out of the room. Control modules 101 may also be configured to provide power to medication delivery modules 100, when coupled with one another (e.g., via a physical connector or plug). In some implementations, medication delivery modules 100 may be configured to operate autonomously from control modules 101, at least for a period of time. Accordingly, medication delivery modules 100 may include batteries or any other type of dedicated power supply that enable them to deliver medication even when they are decoupled from a control module 101 in an IS 150.

In some implementations, medication delivery module 100-1 may be handed over from control module 101-1 in IS 150-1, to control module 101-2 in IS 150-2. This may be the case, for example, when patient 160 is to be removed from a room onto gurney 172 for transport, and IS 150-1 remains attached to rack 140. In some implementations, the handover from first control module 101-1 to second control module 101-2 is executed when a communication between control module 101-1 and medication delivery module 100-1 is lost, or when control module 101-1 is off-line, or turned off (e.g. due to a power failure, or any other error state in the control module).

Each of control modules 101 includes a processor 112 and a memory 120. Memory 120 may include commands and instructions, which when executed by processor 112, cause control modules 101 to perform at least partially some of the steps included in methods consistent with the present disclosure. More specifically, memory 120 in control modules 101 stores clinical information related to the medication delivery. Control modules 101 may receive device information from input received at a physical input interface of IS 150 (e.g., a touch-screen), or may be configured to receive information from a remote server.

Furthermore, control module 101 communicates with the attached medication delivery modules 100 to transmit and receive instructions and data regarding the delivery of medication to patient 160. In some implementations, a control module 101 is configured to receive data from medication delivery module 100 regarding an ongoing medication delivery, and provides a visual status (e.g., a progress report) of the medication delivery (e.g., for a nurse or other medication personnel) through a display 110.

Control modules 101 may include antennas 175-1 and 175-2 (hereinafter, collectively referred to as "antennas 175") for wireless communication with one another, with a central server in a centralized location, or with one or more of medication delivery modules 100. Accordingly, control modules 101 may also include a communications module coupled to processor 112, configured to control and drive antennas 175. Control modules 101 and medication delivery modules 100 may communicate via a Bluetooth, Wi-Fi, or any other radio-frequency protocol. Accordingly, control modules 101 may be configured to process data from medication delivery modules 100 and store a medication delivery progress update in memory 120. In some implementations, other characteristics of the fluid relevant for a medication delivery or infusion may be stored by control modules 101 in memory 120.

In some implementations, medication delivery module 100-1 includes a container 143 having a fluid 170, which is the medication to be delivered to patient 160. In some implementations, medication delivery module 100-1 may include a fluid control system 145 (e.g., an infusion pump) to provide controlled delivery of fluid 170 to patient 160. Medication delivery modules 100-1 may include a memory 151 storing instructions which, when executed by a processor 152, cause medication delivery module 100-1 to perform, at least partially, steps in methods as disclosed herein. More generally, each one of medication delivery modules 100 may include at least one of container 143 (including fluid 170), fluid control system 145, memory 151 and processor 152. Accordingly, each of delivery modules 100 may include a different medication within fluid 170, according to a given medication order or prescription for patient 160.

In some implementations, IS 150-1 includes an intravenous delivery system, and fluid 170 may include an intravenous fluid to be administered to patient 160 through a blood vessel. Accordingly, fluid 170 may include blood, plasma, or a medication. Fluid 170 may be any liquid suitable for intravenous delivery. Common intravenous liquids include crystalloids (e.g., saline, Lactated Ringers, glucose, dextrose), colloids (e.g., hydroxyethyl starch, gelatin), liquid medications, buffer solutions, and blood products (e.g., packed red blood cells, plasma, clotting factors) or blood substitutes (e.g., artificial blood) that are desired to be injected intravenously to a patient 160.

Medication delivery module 100-1 is mechanically coupled with fluid line 130 and is configured to provide the fluid flow (e.g., through a pump 145) and to perform multiple measurements of the fluid flow. In some implementations, medication delivery module 100-1 is configured to measure fluid pressure, fluid flow rate, a presence and amount of air within the fluid, a fluid temperature, and a fluid conductivity of the fluid flow. A fluid line 130 carries fluid 170 from IS 150-1 to patient 160.

In some implementations, control modules 101 may provide an alarm to a centralized system when a bubble count in medication delivery module 100 becomes higher than a threshold, or an occlusion is detected along fluid line 130.

In some implementations, control module 101 provides medication delivery module 100 at least the dynamic part of the clinical information, including the total amount of medication to be delivered, the rate, the time to start delivery, and the time to stop, or pause, the medication delivery. Medication delivery module 100 provides, to control module 101, a status of how far it has progressed to a certain delivery goal. Further, in some implementations, medication delivery module 100 stores at least a portion of the clinical information and a status of the medication delivery in memory 151.

Figure 2:
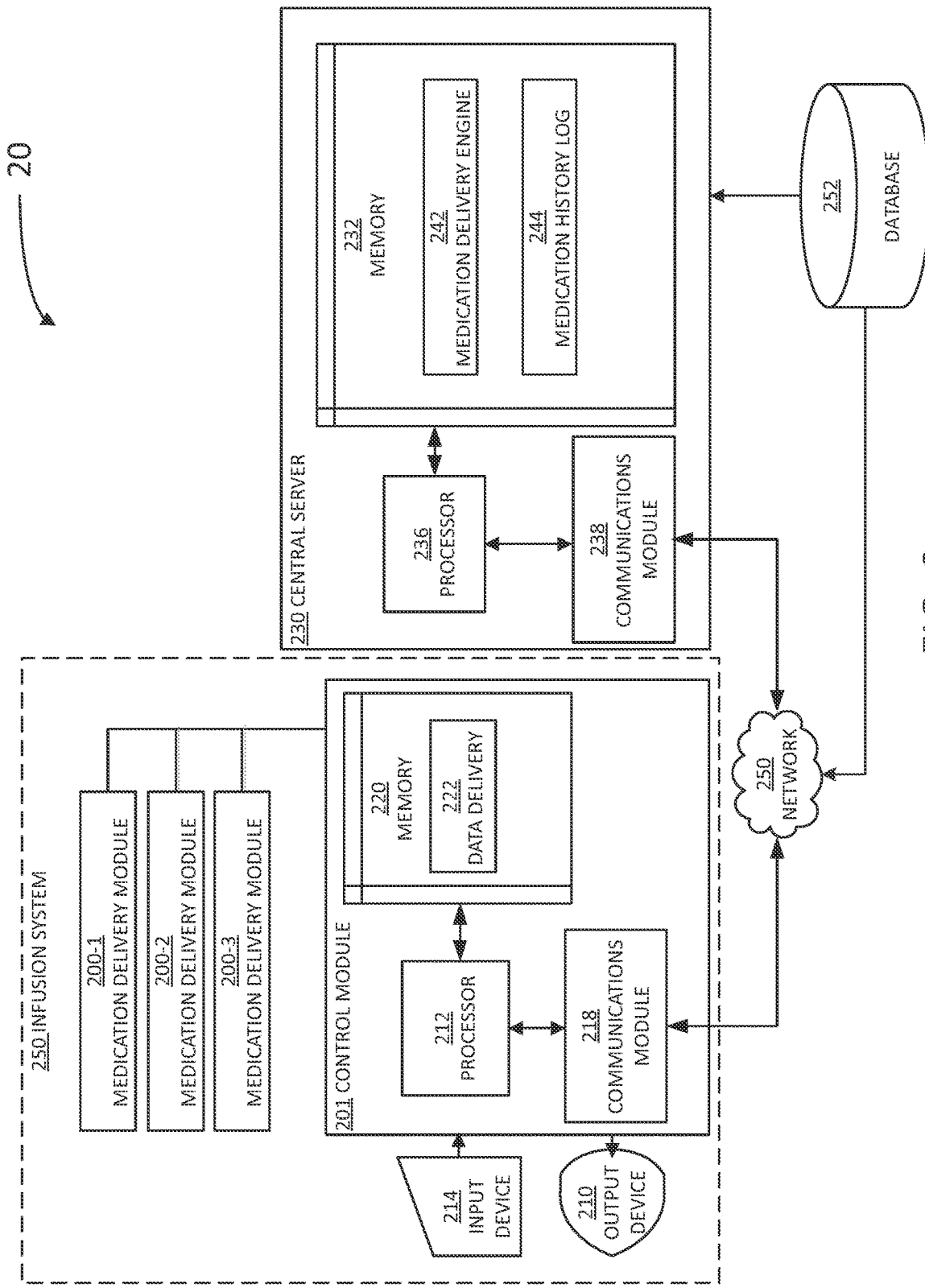
FIG. 2 illustrates a control module configured to control a medication delivery module and a central server communicatively coupled through a network, according to some implementations.

FIG. 2 illustrates an architecture 20 for delivering medication to a patient, according to some implementations. Architecture 20 includes an IS 250 communicatively coupled with a central server 230 through a network 250. IS 250 includes a control module 201 configured to control one or more medication delivery modules 200-1, 200-2, and 200-3 (hereinafter, collectively referred to as "medication delivery modules 200", e.g., medication delivery modules 100), and a central server 230. In some implementations, control module 201 and central server 230 are communicatively coupled through a network 250. Control module 201 is coupled with an input device 214 and an output device 210 to receive instructions from and provide results to a user. Accordingly, input device 214 may include a keyboard, a mouse, a pointer, a microphone, or a touchscreen device, and output device 210 may include a screen, a video display, a speaker, or a printer. In that regard, some implementations may include input device 214 and output device 210 as part of the same touch-screen display (e.g., display 110).

Control module 201 includes a processor 212 and a memory 220. Memory 220 may also include a data delivery application 222, storing instructions which, when executed by processor 212, cause control module 201 to perform, at least partially, steps in methods as disclosed herein. Further, control module 201 may include a communications module 218 configured to communicate with central server 230 through network 250. Likewise, central server 230 may include a communications module 238 configured to communicate with control module 201 through network 250. Central server 230 includes a processor 236 and a memory 232. Memory 232 may include a medication delivery engine 242 and a medication history log 244. Accordingly, in some implementations, medication delivery engine 242 stores instructions which, when executed by processor 236, cause central server 230 to perform, at least partially, steps in methods as disclosed herein. For example, processor 236 may execute some instructions in medication delivery engine 242 that provide instructions to one of medication delivery modules 200 and to communicate data with control module 201 through delivery data application 222.

In some implementations, central server 230 is coupled with a database 252 to store medication history log 244 and other information relevant to medication delivery engine 242 and to the control and data of medication delivery module 200. As shown in the figure, IS 250 may also have access to database 252 to store or retrieve information (e.g., related to medication history log 244).

Figure 3:
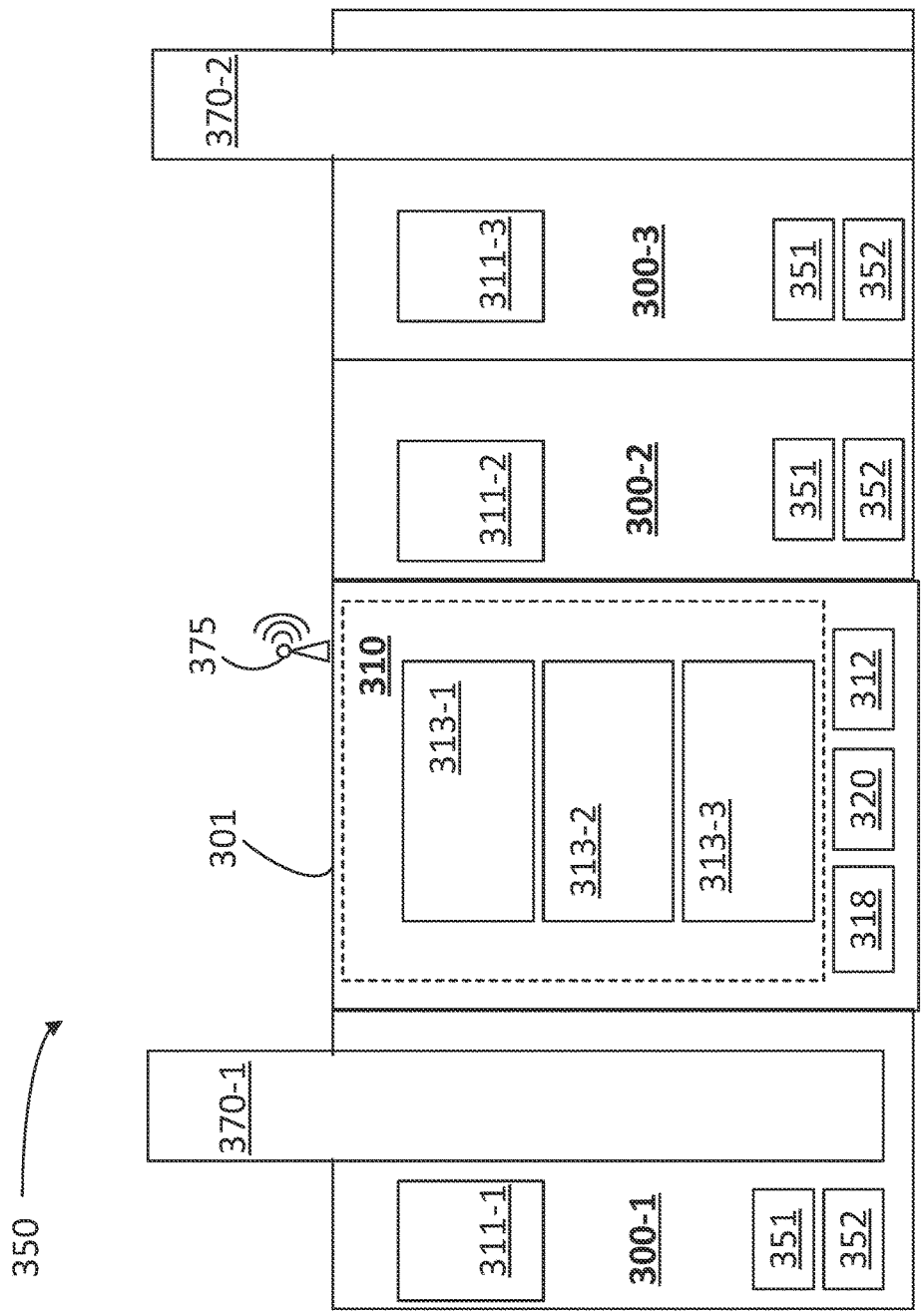
FIG. 3 illustrates a patient care unit including a main display mirroring individual module screens, according to some implementations.

FIG. 3 illustrates an IS 350 including a control module 301 expanded with a medication delivery module 300-1 that is configured to deliver a fluid 370-1, a medication delivery module 300-2, and a medication delivery module 300-3 configured to deliver a fluid 370-2. Medication delivery modules 300-1, 300-2 and 300-3 will be collectively referred to, hereinafter, as "medication delivery modules 300" (e.g., medication delivery modules 100 and 200). Each of medication delivery modules includes a memory 351 storing instructions and a processor 352 configured to execute the instructions to cause medication delivery module 100 to perform at least partially some of the steps in methods as disclosed herein (e.g., memory 151 and processor 152). Each of medication delivery modules 300 includes a module display 311-1, 311-2 and 311-3 (hereinafter, collectively referred to as "module displays 311") respectively, to provide an update of the medication delivery status and current settings to a user (e.g., a healthcare provider or nurse). In some implementations, module displays 311 may be configured as touch-screen displays for receiving user input. Control module 301 includes a main display 310 (e.g., display 110) configured to provide at least some of the medication delivery information retrieved from medication delivery modules 300. In that regard, main display 310 may include individual channel cards 313-1, 313-2, and 313-3 (hereinafter, collectively referred to as "individual channel cards 313") to mirror module displays 311, including at least some display information from each of module displays 311, respectively. Likewise to module displays 311, main display 310 may also be configured as a touch-screen display for receiving user input.

Control module 301 includes a memory 320 storing instructions and a processor 312 configured to execute the instructions to cause control module 301 to perform at least partially some of the steps in methods as disclosed herein. In some implementations, control module 301 also includes a communications module 318 and an antenna 375, configured to communicate wirelessly with a control module (e.g., in a second IS), or with a central server through a network (e.g., central server 230 and network 250).

In some implementations, one of medication delivery modules 300 may be removed from IS 350 to be installed or plugged-in to a second IS. Accordingly, in some implementations the fluid infusion information in the corresponding module display 311 may still be displayed while the medication delivery module 300 is unplugged from IS 350.

Figure 4:
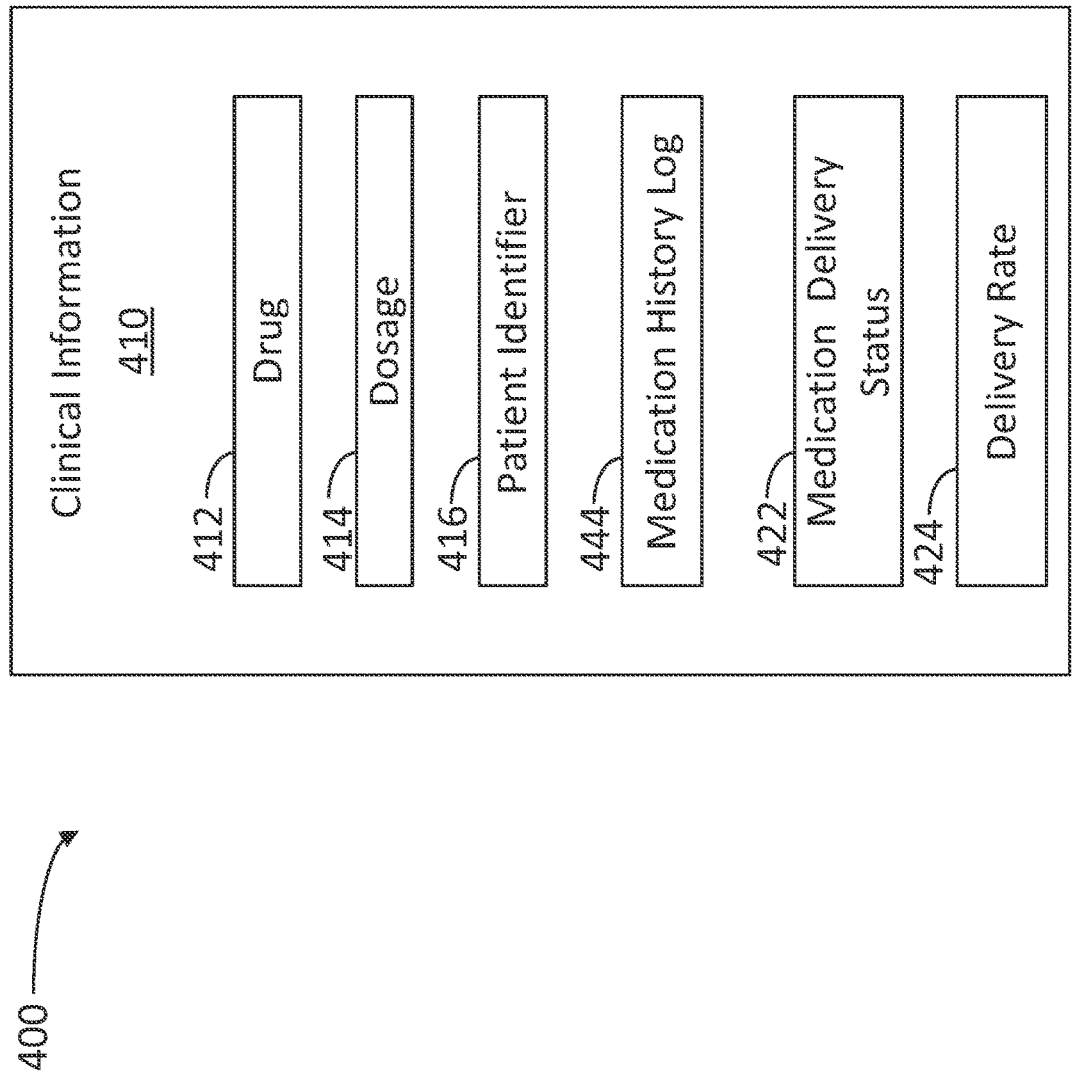
FIG. 4 illustrates a medication delivery data structure shared between a medication delivery module, a control module, and a central server, according to some implementations.

FIG. 4 illustrates a medication delivery data structure 400 shared between a medication delivery module, a control module, and a central server, according to some implementations (e.g., medication delivery modules 100, 200 or 300, control module 101, 201 or 301 and central server 230). Medication delivery data structure 400 includes a clinical information 410. Clinical information 410 may include a drug type 412, a dosage 414, and a patient identifier 416. Clinical information 410 may also include a medication history log 444 (e.g., medication history log 244), a medication delivery status 422, and a medication delivery rate 424. In some implementations, a control module (e.g., control modules 101, 201 or 301) may be configured by central server 230 to handle medication delivery to one or more patients identified by patient identifier 416.

A medication delivery module as disclosed herein (e.g., medication delivery modules 100, or 300) are configured to store at least part of medication delivery data structure 400 in memories 151 and 351, respectively. Furthermore, ISs 150, 250, and 350 may be configured to store at least a portion of delivery data structure 400 in memories 151, 220, and 320, for each medication delivery module 100, 200, or 300, respectively. Also, a central server in communication with the medication delivery module and with the IS may store at least a portion of delivery data structure 400 in a memory, a medication history log, or a database (e.g., central server 230, memory 232, medication history log 244, and database 252).

Accordingly, in some implementations, the medication delivery module may not store clinical information for a patient, but instead, on connecting to an IS (or control module), sends it to the IS to be sent to the server. The module provides a module identifier (e.g., a serial number or other identifier) of the module to the IS, together with clinical information and, in some implementations, infusion data (e.g., rate, volume, amount infused, length of time elapsed, etc.). The IS then sends the clinical information to the server to be stored in association with the module identifier. When the module is connected to a new IS, the new IS receives the module identifier from the module and reports the module identifier of the newly-connected module to the server. The server then retrieves the stored information based on the module identifier and provides the new IS with the stored information (including information on what the module was doing last). In this manner, the new IS may perform certain validations and instruct the module to continue the delivery of the medication (if the infusion is not already underway).

Figure 5:
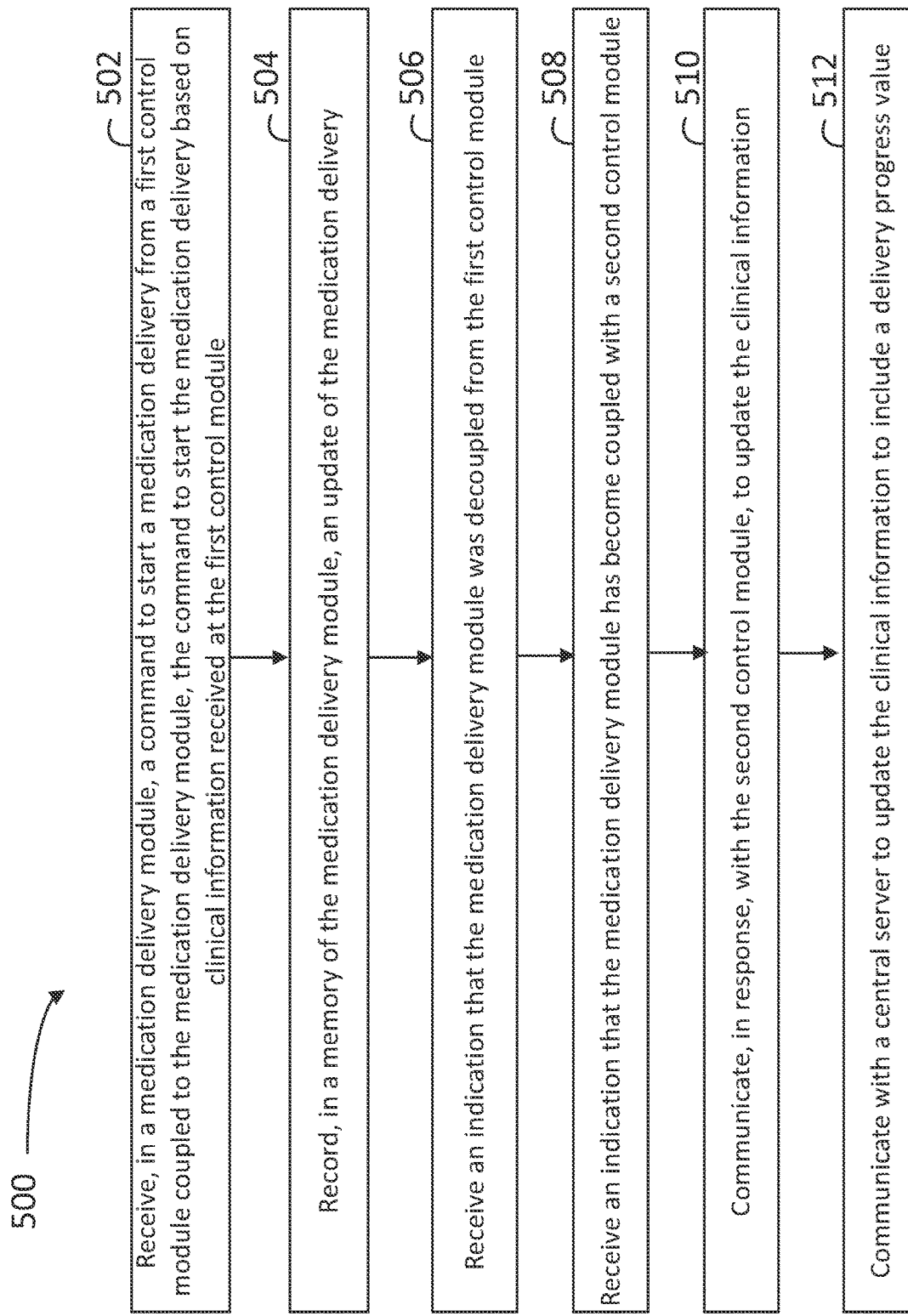
FIG. 5 illustrates a flowchart in a method for delivering medication to a patient, according to some implementations.

FIG. 5 illustrates a flowchart in a method 500 for delivering medication to a patient, according to some implementations. Method 500 may be performed at least partially by a first and a second ISs hosting one or more medication delivery modules in a control module (e.g., ISs 150, 250, and 350, control modules 101, 201 and 301, and medication delivery modules 100, 200 and 300), while communicating with one or more central servers (e.g., server 230). At least some of the steps in method 500 may be performed by a computer having a processor executing commands stored in a memory of the computer (e.g., processors 112, 152, 212, 236, 312 and 352, memories 120, 151, 220, 232, 320 and 351). In some implementations, steps as disclosed in method 500 may include retrieving, editing, and/or storing files in a database that is part of, or is communicably coupled to, the central server (e.g., medication history log 244 and database 252). Methods consistent with the present disclosure may include at least some, but not all, of the steps illustrated in method 500, performed in a different sequence. Furthermore, methods consistent with the present disclosure may include at least two or more steps as in method 500 performed overlapping in time, or almost simultaneously.

Step 502 includes receiving, in a medication delivery module, a command to start a medication delivery from a first control module coupled to the medication delivery module. The command to start the medication delivery may be based on clinical information received at the first control module. In some implementations, the command to start a medication delivery may include configuration settings for a medication infusion such as a dosage, a delivery rate (e.g., infusion pump rate) and other clinical information. In some implementations, step 502 includes starting the medication delivery to the patient. In some implementations, step 502 may be performed by a clinician starting the medication delivery module (e.g., a nurse or a physician through a touch-screen display in the medication delivery module).

Step 504 includes recording, in a memory of the medication delivery module, an update of the medication delivery. In some implementations, step 504 includes recording the clinical information associated with the medication delivery in a memory (e.g., memories 120, 151, 220, 232, 320 and 351). In some implementations, in step 504 the medication delivery module simply records, without validation, the clinical information in the memory. In some implementations, step 504 may include recording the clinical information in a memory of the central server (e.g., central server 230, and memory 232). In some implementations, step 504 includes validating the clinical information (e.g., verifying that a drug and dosage to be delivered matches the fluid content of a container in the medication delivery module). In some implementations, the medication delivery module may be configured to perform step 504 when level of a battery in the medication delivery module has reached a pre-selected critical value. In some implementations step 504 is performed by the medication delivery module performing the medication delivery, and the update of the medication delivery is stored in memories 351. In some implementations, step 504 may be performed by the control module and the update of the medication delivery is stored in memories 120. In some implementations, step 504 may include stop delivering the medication when a dose level provided by the control module or included in the clinical information has been reached. In some implementations, step 504 may include stopping the medication delivery even when the medication delivery module is decoupled from the first control module and has continued delivering medication thereafter.

Step 506 includes receiving an indication that the medication delivery module was decoupled from the first control module. In some implementations, step 506 further includes the medication delivery module continuing the medication delivery instructed by the first control module for a period of time, while the medication delivery module is decoupled from the first control module. The period of time may be determined by the lifetime of a battery in the medication delivery module. In some implementations, step 506 further includes storing by the medication delivery module in a memory a medication delivery log comprising a medication delivery status, and including the medication delivery log in the clinical information. In some implementations, step 506 further includes selecting the second control module according to a quality of a wireless signal received from the second control module. In some implementations, the medication delivery condition includes one of a stop of the first control module, or a communication breakdown with the first control module, and step 506 further includes issuing an alert to the second control module and to the central server that the first control module stopped, or that a communication with the first control module is broken.

Step 508 includes receiving an indication that the medication delivery module has become coupled with a second control module. In some implementations, step 508 may include waiting a confirmation from the second control module that the clinical information associated with the medication delivery from the medication delivery module is valid, prior to resume the medication delivery. In some implementations, step 508 may include prompting a clinician, nurse, or other medical personnel, to validate the clinical information before continuing with the medication delivery. In some implementations, step 508 includes requesting the central server to validate the clinical information. In some implementations, step 508 includes performing error checks for the medication delivery. In some implementations, step 508 may include verifying that an infusion parameter in the clinical information is consistent with a setting in a medication delivery module. In some implementations, step 508 may include measuring a property of a fluid to be delivered, the property comprising one of a temperature, a bubble concentration, or a presence of a downstream occlusion, and logging a value of the property in a history log that is part of the clinical information. In some implementations, step 508 may include issuing an alert to the second control module and to the central server when an error is detected in the medication delivery, or that the level of the battery in the medication delivery module has reached the pre-selected critical value. In some implementations, step 508 includes receiving an indication that a connector terminal of the medication delivery module has been inserted into a plug-in port or a socket in the second control module.

Step 510 includes communicating, in response, with the second control module, to update the clinical information. In some implementations, step 510 includes automatically communicating, by the medication delivery module, with the second control module. In some implementations, step 510 includes providing, by the medication delivery module, the commands and setting configurations received from the first control module to start the medication delivery, to the second control module. Further, step 510 may include providing to the second control module clinical information related to the medication delivery, including a current status of the medication delivery, and providing to the second control module a display information as to font size, type, and specific clinical information to be displayed in a display of the control module, pertaining to the medication delivery. In some implementations, step 510 includes resuming medication delivery under the second control module. In some implementations, step 510 is performed when the clinical information is validated, or when the first control module has stopped. In some implementations, step 510 includes continuing the medication delivery after the first control module is decoupled from the medication delivery module, and even before coupling with the second control module. In some implementations, in step 510 the medication delivery module provides the second control module medication delivery information and informs the second control module that the medication delivery module is ready to start receiving programming commands. Accordingly, step 510 may also include receiving, by the medication delivery module, a confirmation from the second control module of issuing programming commands to resume medication delivery.

Step 512 includes communicating with the central server to update the clinical information to include a delivery progress value. In some implementations, step 512 includes resuming the medication delivery under the second control module when the medication delivery under the first control module has stopped. In some implementations, step 512 also includes storing clinical data associated with the medication delivery in a memory.

Figure 6:
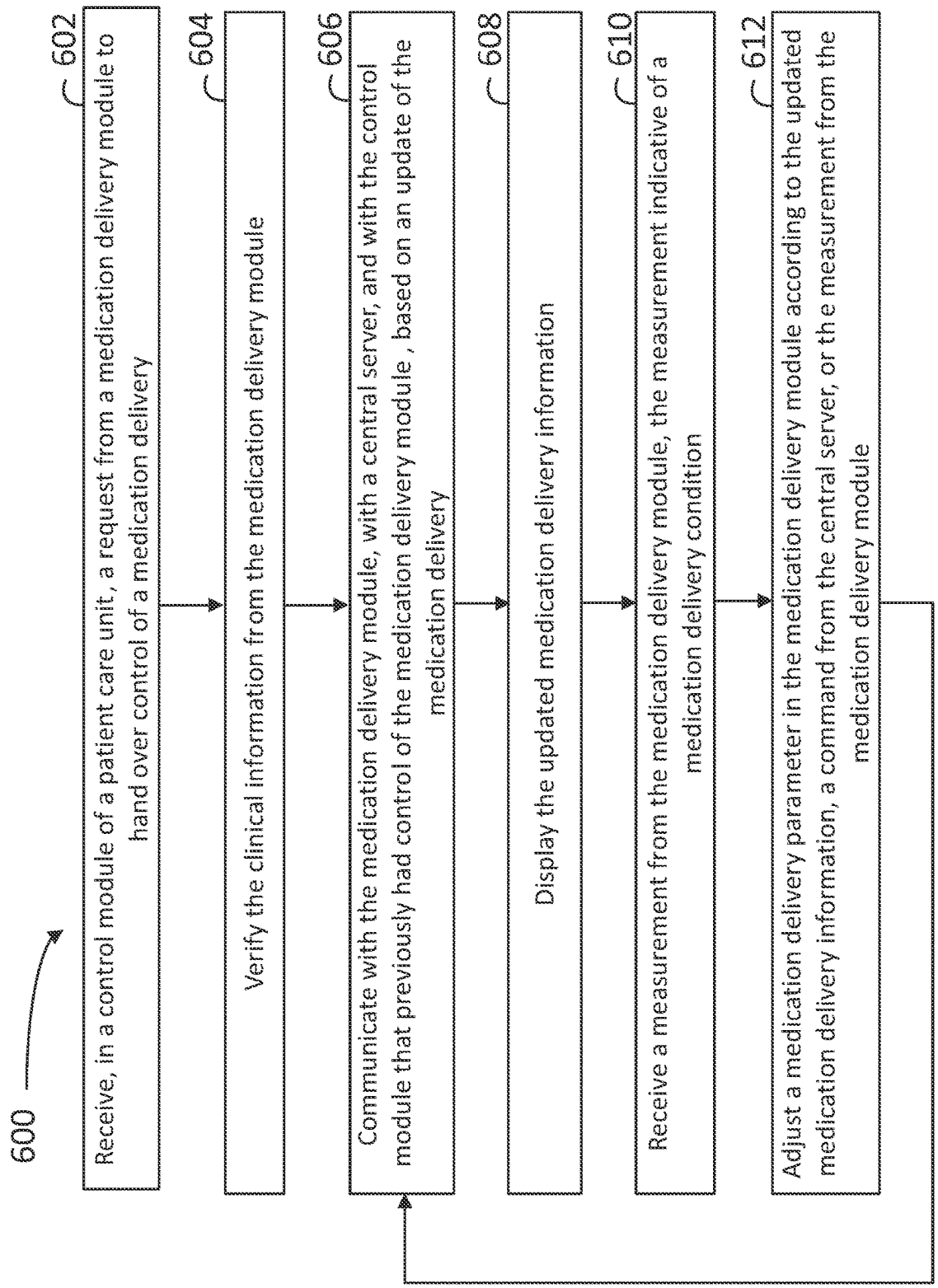
FIG. 6 illustrates a flowchart in a method for swapping control of a medication delivery module when the medication delivery has started, according to some implementations.

FIG. 6 illustrates a flowchart in a method 600 for swapping control of a medication delivery module when a medication delivery has started, according to some implementations. Method 600 may be performed at least partially by a first and a second IS hosting one or more medication delivery modules in a control module (e.g., ISs 150, 250, and 350, control modules 101, 201 and 301, and medication delivery modules 100, 200 and 300), while communicating with one or more central servers (e.g., server 230). At least some of the steps in method 600 may be performed by a computer having a processor executing commands stored in a memory of the computer (e.g., processors 112, 152, 212, 236, 312 and 352, memories 120, 151, 220, 232, 320 and 351). In some implementations, steps as disclosed in method 600 may include retrieving, editing, and/or storing files in a database that is part of, or is communicably coupled to, the central server (e.g., medication history log 244 and database 252). Methods consistent with the present disclosure may include at least some, but not all, of the steps illustrated in method 600, performed in a different sequence. Furthermore, methods consistent with the present disclosure may include at least two or more steps as in method 600 performed overlapping in time, or almost simultaneously.

Step 602 includes receiving, in a control module of a receiving IS, a request from a medication delivery module to assume control of a medication delivery to a patient (e.g., when the patient is being translated and the medication delivery module is being switched from a previous control module of an IS to the control module of the receiving IS). In some implementations, step 602 may include transmitting a serial number of the medication delivery module to the central server, for verification and storage in the medication history log.

Step 604 includes verifying the clinical information from the medication delivery module. In some implementations, step 604 may include requesting the central server to validate the clinical information, by comparing the clinical information with data stored in a medication history log. For example, in some implementations step 604 may include verifying a patient ID, a drug to be delivered, a dosage, and a delivery rate for the medication delivery with data stored in the medication history log in the database or the central server. In some implementations, step 604 includes associating the clinical information in the history log with the serial number of the medication delivery module, in the central server.

Step 606 includes establishing a communication between the control module of the IS receiving the request to assume control and either one of the medication delivery module, the central server, and the control module that previously had control of the medication delivery module, based on an updated medication delivery information. In some implementations, step 606 may include receiving, from the central server, the updated medication delivery information, including information indicative of the actions performed by the medication delivery module prior to coupling to the control module, including updated clinical information.

Step 608 includes displaying the updated medication delivery information in a display in the control module of the IS receiving the request to assume control of the medication delivery module. In some implementations, step 608 may include indicating, in the display, the medication delivery module that is performing the medication delivery associated with the medication delivery information. In some implementations, step 608 may include requesting confirmation from a user (e.g., clinician or nurse) to continue with the medication delivery through the medication delivery module.

Step 610 includes receiving a measurement from the medication delivery module, the measurement indicative of a medication delivery status. For example, the medication delivery status may be 'complete,' incomplete, "canceled," and the like.

Step 612 includes adjusting a medication delivery parameter in the medication delivery module according to the updated medication delivery information, a command from the central server, or the measurement from the medication delivery module.

Figure 7:
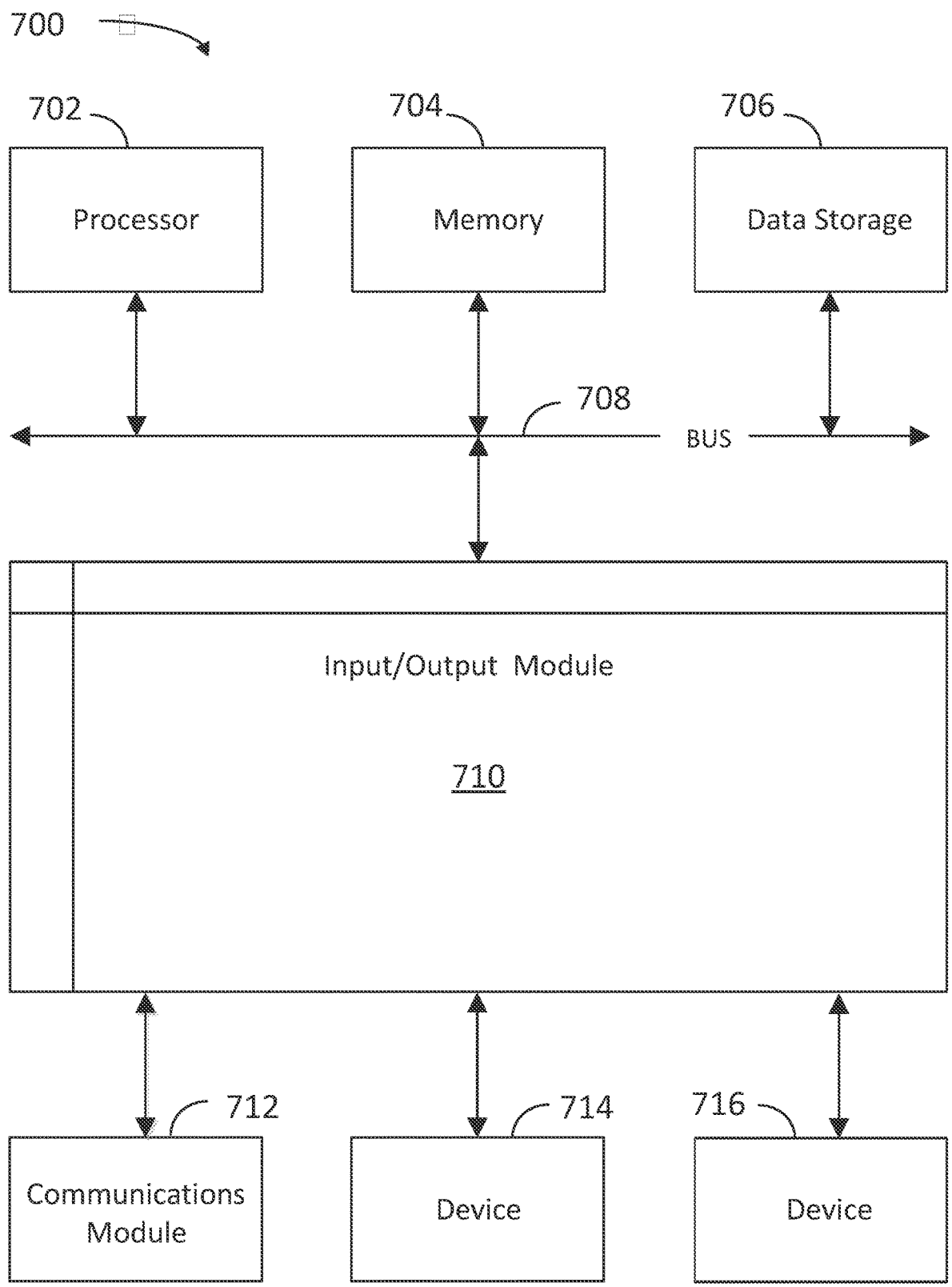
FIG. 7 is a block diagram illustrating an example computer system with which the client and server of FIGS. 1 and 2, and the methods of FIGS. 5 and 6 can be implemented, according to some implementations.

FIG. 7 is a block diagram illustrating an example computer system 700 with which the client and server of FIGS. 1 and 2, and the methods of FIGS. 5 and 6 can be implemented, according to some implementations.

Computer system 700 (e.g., medication delivery module 100 and control module 101) includes a bus 708 or other communication mechanism for communicating information, and a processor 702 (e.g., processors 112, 152, 212, and 236) coupled with bus 708 for processing information. By way of example, the computer system 700 may be implemented with one or more processors 702. Processor 702 may be a general-purpose microprocessor, a micro control module, a Digital Signal Processor (DSP), an Application Specific Integrated Circuit (ASIC), a Field Programmable Gate Array (FPGA), a Programmable Logic Device (PLD), a control module, a state machine, gated logic, discrete hardware components, or any other suitable entity that can perform calculations or other manipulations of information.

Computer system 700 can include, in addition to hardware, a code that creates an execution environment for the computer program in question, e.g., code that constitutes processor firmware, a protocol stack, a database management system, an operating system, or a combination of one or more of them stored in an included memory 704 (e.g., memories 120, 151, 220, and 232), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 708 for storing information and instructions to be executed by processor 702. The processor 702 and the memory 704 can be supplemented by, or incorporated in, a special purpose logic circuitry.

The instructions may be stored in the memory 704 and implemented in one or more computer program products, i.e., one or more modules of computer program instructions encoded on a computer readable medium for execution by, or to control the operation of, the computer system 700, and according to any method well known to those skilled in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and xml-based languages. Memory 704 may also be used for storing temporary variable or other intermediate information during execution of instructions to be executed by processor 702.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 700 further includes a data storage device 706, such as a magnetic disk or optical disk, coupled to bus 708 for storing information and instructions. Computer system 700 may be coupled via input/output module 710 to various devices. Input/output module 710 can be any input/output module. Exemplary input/output modules 710 include data ports such as USB ports. Input/output module 710 is configured to connect to a communications module 712. Exemplary communications modules 712 (e.g., communications modules 218 and 238) include networking interface cards, such as Ethernet cards and modems. In certain aspects, input/output module 710 is configured to connect to a plurality of devices, such as an input device 714 (e.g., input device 214) and/or an output device 716 (e.g., output device 210). Exemplary input devices 714 include a keyboard and a pointing device, e.g., a mouse or a trackball, by which a user can provide input to the computer system 700. Other kinds of input devices 714 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Exemplary output devices 716 include display devices, such as an LCD (liquid crystal display) monitor, for displaying information to the user.

According to one aspect of the present disclosure, medication delivery modules 100, control modules 101, and server 230 can be implemented using a computer system 700 in response to processor 702 executing one or more sequences of one or more instructions contained in memory 704. Such instructions may be read into memory 704 from another machine-readable medium, such as data storage device 706. Execution of the sequences of instructions contained in main memory 704 causes processor 702 to perform the process steps described herein. One or more processors in a multi-processing arrangement may also be employed to execute the sequences of instructions contained in memory 704. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. The communication network (e.g., network 250) can include, for example, any one or more of a LAN, a WAN, the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computer system 700 can include clients and servers. A client and server are generally remote from each other and typically interact through a communication network. The relationship of client and server arises by virtue of computer programs running on the respective computers and having a client-server relationship with each other. Computer system 700 can be, for example, and without limitation, a desktop computer, laptop computer, or tablet computer. Computer system 700 can also be embedded in another device, for example, and without limitation, a mobile telephone, a PDA, a mobile audio player, a Global Positioning System (GPS) receiver, a video game console, and/or a television set top box.

The term "machine-readable storage medium" or "computer readable medium" as used herein refers to any medium or media that participates in providing instructions to processor 702 for execution. Such a medium may take many forms, including, but not limited to, non-volatile media, volatile media, and transmission media. Non-volatile media include, for example, optical or magnetic disks, such as data storage device 706. Volatile media include dynamic memory, such as memory 704. Transmission media include coaxial cables, copper wire, and fiber optics, including the wires that include bus 708. Common forms of machine-readable media include, for example, floppy disk, flexible disk, hard disk, magnetic tape, any other magnetic medium, CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (e.g., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the terms "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any implementation described herein as "exemplary" is not necessarily to be construed as preferred or advantageous over other implementations.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and implementations of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A medication delivery system, comprising:
an infusion pump;
a non-transitory memory storing instructions; and
one or more processors coupled with the non-transitory memory and configured to execute the instructions to cause the medication delivery system to:
receive an indication that an infusion module became physically coupled, via a connector, to the medication delivery system;
operate the medication delivery system as a control module for the infusion module when the infusion module is coupled to the medication delivery system via the connector;

receive, when and based on the infusion module becoming physically coupled to the medication delivery system, clinical information pertaining to a medication delivery facilitated by the infusion module and received by the infusion module when the infusion module was physically coupled to a different medication delivery system before the infusion module became physically coupled to the medication delivery system, and delivery data obtained by the infusion module after the infusion module was physically decoupled from the different medication delivery system and before the infusion module became physically coupled to the medication delivery system; and facilitate operation of the infusion module to continue the medication delivery based on the clinical information and the delivery data.

2. The medication delivery system of claim 1, further comprising:

a physical input interface, wherein the one or more processors further cause the medication delivery system to:

receive device information via the physical input interface regarding the medication delivery facilitated by the infusion module; and transmit the received device information to the infusion module for delivery of the medication delivery facilitated by the infusion module.

3. The medication delivery system of claim 1, wherein the one or more processors further cause the medication delivery system to, before causing the infusion module to continue the medication delivery:

provide, for display on a display device associated with the medication delivery system, an indication of the medication delivery and at least a portion of the clinical information; and request confirmation from a user to continue with the medication delivery using the infusion module.

4. The medication delivery system of claim 1, wherein the different medication delivery system comprises an infusion pump and is operated as a control module.

5. The medication delivery system of claim 1, wherein the one or more processors further cause the medication delivery system to:

transmit, by the medication delivery system, one or more commands or setting configurations for starting the medication delivery.

6. The medication delivery system of claim 1, wherein the one or more processors further cause the medication delivery system to:

receive the clinical information and the delivery data from a server, wherein the delivery data comprises progress information pertaining to a medication of the medication delivery, the medication being administered by the infusion module.

7. The medication delivery system of claim 1, wherein the one or more processors further cause the medication delivery system to:

update the delivery data to include a delivery progress of a medication while the infusion module is coupled to the medication delivery system; and provide the updated delivery data to a server.

8. The medication delivery system of claim 1, wherein the one or more processors further cause the medication delivery system to:

validate the clinical information responsive to the indication that the infusion module became physically coupled to the medication delivery system; and send, by the medication delivery system, a command to the infusion module to continue the medication delivery responsive to validating the clinical information.

9. The medication delivery system of claim 8, wherein the one or more processors further cause the medication delivery system to:

validate the clinical information based on verifying a patient identifier, a drug to be delivered, a dosage, or a delivery rate for the medication delivery.

10. The medication delivery system of claim 9, wherein the one or more processors further cause the medication delivery system to:

verify the patient identifier, the drug to be delivered, the dosage, or the delivery rate with data stored in a medication history log stored at a server or in a database associated with the server.

11. A method, comprising:

receiving, under control of a medication delivery system, an indication that an infusion module became physically coupled, via a connector, to the medication delivery system;

operating the medication delivery system as a control module for the infusion module when the infusion module is coupled to the medication delivery system via the connector;

receiving, when and based on the infusion module becoming physically coupled to the medication delivery system, clinical information pertaining to a medication delivery facilitated by the infusion module and received by the infusion module when the infusion module was physically coupled to a different medication delivery system before the infusion module became physically coupled to the medication delivery system, and delivery data obtained by the infusion module after the infusion module was physically decoupled from the different medication delivery system and before the infusion module became physically coupled to the medication delivery system; and facilitating operation of the infusion module to continue the medication delivery based on the clinical information and the delivery data.

12. The method of claim 11, further comprising:

receiving, via a physical input interface of the medication delivery system, device information regarding the medication delivery facilitated by the infusion module; and transmitting the received device information to the infusion module for delivery of the medication delivery facilitated by the infusion module.

13. The method of claim 11, further comprising, before causing the infusion module to continue the medication delivery:

providing, for display on a display device associated with the medication delivery system, an indication of the medication delivery and at least a portion of the clinical information; and requesting confirmation from a user to continue with the medication delivery using the infusion module.

14. The method of claim 11, wherein the different medication delivery system comprises an infusion pump and is operated as a control module.

15. The method of claim 11, further comprising:
transmitting, by the medication delivery system, one or more commands or setting configurations for starting the medication delivery.

16. The method of claim 11, further comprising:
receiving the clinical information and the delivery data from a server, wherein the delivery data comprises progress information pertaining to a medication of the medication delivery, the medication being administered by the infusion module.

17. The method of claim 11, further comprising:
updating the delivery data to include a delivery progress of the medication while the infusion module is coupled to the medication delivery system; and
providing the updated delivery data to a server.

18. The medication delivery system of claim 11, further comprising:
validating, responsive to indication that a infusion module became physically coupled to the medication delivery system, the clinical information; and
sending, by the medication delivery system, a command to the infusion module to continue the medication delivery responsive to validating the clinical information.

19. The medication delivery system of claim 18, further comprising:
validating the clinical information based on verifying a patient identifier, a drug to be delivered, a dosage, or a delivery rate for the medication delivery.

20. A medication delivery device, comprising:
an infusion pump; and
a control module configured to:
 receive an indication that an infusion module became physically coupled, via a connector, to the medication delivery device;
 operate the medication delivery device as a controller for the infusion module when the infusion module is coupled to the medication delivery device via the connector;
 receive, when and based on the infusion module becoming physically coupled to the medication delivery device, clinical information pertaining to a medication delivery facilitated by the infusion module and received by the infusion module when the infusion module was physically coupled to a different medication delivery device before the infusion module became physically coupled to the medication delivery device, and delivery data obtained by the infusion module after the infusion module was physically decoupled from the different medication delivery device and before the infusion module became physically coupled to the medication delivery device; and
 cause the infusion module to continue the medication delivery based on the clinical information and the delivery data.

* * * * *